United States Patent [19]

Gold et al.

[11] 4,253,931

[45] Mar. 3, 1981

[54] ELECTRODE SPUTTERING PROCESS FOR EXHAUST GAS OXYGEN SENSOR

[75] Inventors: Terry J. Gold, Flint, Mich.; Kurt D. Humphrey, Rolla, Mo.; Keith A. Penney, Davison, Mich.; Robert J. Smith, Flint, Mich.; Randy L. Voto, Flint, Mich.; Ralph V. Wilhelm, Jr., Flint, Mich.

[73] Assignee: General Motors Corporation, Detroit, Mich.

[21] Appl. No.: 98,726

[22] Filed: Nov. 30, 1979

Related U.S. Application Data

[63] Continuation-in-part of Ser. No. 30,748, Apr. 17, 1979, abandoned.

[51] Int. Cl.$^3$ .............................................. C23C 15/00
[52] U.S. Cl. ............................ 204/192 SP; 204/195 S
[58] Field of Search ........... 204/192 C, 192 SP, 195 S

[56] References Cited

U.S. PATENT DOCUMENTS

| | | | |
|---|---|---|---|
| 3,978,006 | 8/1976 | Topp et al. | 252/477 R |
| 4,021,326 | 3/1977 | Pollner et al. | 204/195 S |
| 4,116,883 | 9/1978 | Rhodes | 252/463 |
| 4,136,000 | 1/1979 | Davis et al. | 204/195 S |

OTHER PUBLICATIONS

L. I. Maissel et al., *Handbook of Thin Film Technology*, McGraw-Hill Book Co., New York, 1970, pp. 4-26 to 4-31.

*Primary Examiner*—T. Tung
*Assistant Examiner*—William Leader
*Attorney, Agent, or Firm*—Robert J. Wallace

[57] ABSTRACT

A method of sputtering platinum onto a vitrified zirconia thimble to form an exhaust electrode for an electrochemical-type exhaust gas oxygen sensor. The electrode is sputtered under an atmosphere consisting essentially of more than about 50% oxygen and/or nitrogen by volume. Sensors having low symmetrical transition times are produced.

5 Claims, No Drawings

ELECTRODE SPUTTERING PROCESS FOR EXHAUST GAS OXYGEN SENSOR

CROSS REFERENCE TO RELATED PATENT APPLICATION:

This patent application is a continuation-in-part of U.S. patent application Ser. No. 030,748, filed Apr. 17, 1979, now abandoned.

FIELD OF THE INVENTION

This invention relates to solid electrolyte electrochemical-type exhaust gas oxygen sensors. It more particularly relates to a sputtering process for depositing a platinum exhaust gas electrode onto vitrified zirconia thimbles for such sensors.

BACKGROUND OF THE INVENTION

A typical automotive-type solid electrolyte exhaust gas oxygen sensor is disclosed in U.S. Pat. No. 3,844,920 Burgett et al. It has a zirconia sensing element shaped as a tapered thimble. One thimble end is open and has a circumferential flange. The other end is closed and forms the most active part of the element. The interior and exterior of the thimble have separate porous electrode coatings of platinum or the like. The inner electrode is exposed to a source of oxygen, such as air or mixed metal oxide, for establishing a reference potential. The electrode has generally been formed by painting on a coating of platinum ink onto the zirconia thimble, drying the coating, and then firing the coated thimble at an elevated temperature. An improved technique by which it can be applied to the thimble is described and claimed in the copending U.S. patent application Ser. No. 080,449, entitled "Reference Electrode Process for Exhaust Gas Oxygen Sensor" that was filed Oct. 1, 1979 in the name of John Trevorrow and assigned to the assignee of this invention.

The outer electrode is exposed to the exhaust gas for establishing a potential determined by exhaust gas oxygen concentration. The outer electrode could be a porous thick film of platinum, like the inner electrode. However, it is preferred that this outer electrode be a thin film, applied by evaporation, sputtering, chemical vapor deposition or other such thin film deposition techniques. On the other hand, it has been difficult to consistently reproduce desirable properties, such as porosity and electrical parameters in the thin film electrodes. As a result, yields of satisfactory electrode properties have been limited, and various ancillary treatments have been developed to improve them. For example, U.S. Pat. No. 3,978,006 Topp et al discloses heating the solid electrolyte body after electrode deposition, to form pores in the electrode coating if it is not porous as deposited. U.S. Pat. No. 4,136,000 Davis et al discloses treating the electroded sensor element chemically and electrolytically to enhance sensor properties. U.S. patent application Ser. No. 89,264, entitled "Exhaust Electrode Process for Exhaust Gas Oxygen Sensor", filed on Oct. 29, 1979 in the names of Terry J. Gold et al and assigned to the assignee of this invention, discloses an improved sputtering process for producing porous platinum electrodes as deposited. Sensors having sputtered electrodes produced by the latter process consistently exhibit substantially stable response times of less than 600 milliseconds, particularly if heated once or twice in pure nitrogen at atmospheric pressure to 800° C. for about 45 minutes before they are used. This nitrogen aging treatment is disclosed in U.S. patent application Ser. No. 030,748, entitled "Aging Treatment for Exhaust Gas Oxygen sensor", filed Apr. 17, 1979 in the names of Morris Berg et al and assigned to the assignee of this invention.

We have now found how to sputter platinum electrodes onto zirconia bodies in an even more improved way. We believe it provides improved consistency in electrode porosity and microstructure as deposited. In any event, it provides sensors that are fast and substantially stable as formed. Post-electroding treatments for activation and/or aging are unnecessary to obtain fast acting sensors. Moreover, rich-to-lean and lean-to-rich transition times are more balanced as formed and the sensors exhibit improved controllability. On the other hand, aging can still be beneficial, particularly in increasing the yield of fast acting sensors.

OBJECTS AND SUMMARY OF THE INVENTION

An object of this invention is to provide an improved sputtering process for depositing a platinum exhaust electrode onto a zirconia solid electrolyte body for an electrochemical-type exhaust gas oxygen sensor.

The invention involves sputtering platinum onto zirconia thimbles in an atmosphere preferably consisting essentially of about 65–75% by volume nitrogen and/or oxygen and the balance argon, at a pressure of about 10–20 millitorr. A wide target-thimble spacing of about 3.8 centimeters is used, along with a high sputtering power of about 13–22 watts/cm$^2$ of target area. These latter conditions are the same as those described and claimed in the aforementioned U.S. patent application Ser. No. 89,264.

DESCRIPTION OF THE PREFERRED EMBODIMENTS

This invention is an improvement over the sputtering process described and claimed in the aforementioned U.S. Ser. No. 89,264. It differs primarily in that the discharge gas is chiefly nitrogen and/or oxygen. Somewhere between 50% and 65% by volume nitrogen and/or oxygen is necessary in the discharge gas, to achieve the benefits of this invention. More than about 50% nitrogen and/or oxygen is needed, and about 65% appears to consistently provide the improved results of this invention. However, to insure that these results are consistently obtained, we prefer to employ about 75% by volume nitrogen and/or oxygen and about 25% by volume argon. Increasing the nitrogen and/or oxygen proportion beyond the 75% is unnecessary and may even be counter-productive. The rate of deposition will decrease. Also, film adhesion may decrease and/or strength of the underlying zirconia may not be optimum.

Nitrogen and oxygen appear to be equally effective in producing the advantages of this invention. However, using oxygen requires that the apparatus, particularly the pumping system, be modified to accept it. Otherwise, seals and the like can be attacked, creating safety problems. Accordingly, we prefer to use nitrogen instead of oxygen. Analogously, we expect that other inert gases could be substituted for argon. However, we do not consider it practical to do so.

We believe that the higher sputtering pressure of 10–20 millitorr also insures consistent platinum porosity and microstructure. Below a pressure of about 10 millitorr in the deposition chamber, the coating appears to be less porous. Above about 20 millitorr, deposition rate decreases, deposition in unwanted areas commences, and formation of a desirable porous microstructure may be suppressed.

With the sputtering improvement of this invention over the sputtering process of the aforementioned U.S. Ser. No. 89,264, the neutral atmosphere aging of U.S. Ser. No. 030,747 can be omitted. On the other hand, for reasons hereinafter more fully explained, we may not prefer to omit such aging. One principal advantage of this invention over that of U.S. Ser. No. 89,264 is an improved initial response time, regardless as to subsequent heat treatments. Another advantage is in that this invention generally provides a narrower variation in sensor properties within a given batch that is electroded. This not only reduces mean response time but also reduces the standard deviation from it, which improves yields. It is to be understood, however, that this invention is not known to preclude a gradual sensor deterioration normally attendant to extended sensor use.

Solid electrolyte thimble-like sensing elements for an automotive-type exhaust gas oxygen sensor can be electroded in the following manner. The elements can be tapered thimbles of vitrified zirconia that is partially or fully stabilized in its cubic form by the inclusion of about 4–8 mole percent yttria. Best results have been obtained using partially stabilized zirconia containing about 5 mole percent alumina and 5 mol percent yttria. The thimbles are of the same dimensions and interiorly electroded in the same manner as described in the aforementioned U.S. Ser. No. 030,449. In general, they are about 3–5 cm long. Each thimble is preferably about 3.7 cm long and has a taper of about 3 degrees and 38 minutes. Its wider end is open and surrounded by a circumferential shoulder having an outer diameter of about 1.32 cm. Its closed narrower end is rounded on its outer surface where it has a spherical radius of curvature of about 3 mm. Its diameter near the shoulder is about 0.82 cm. Its diameter near the radius is about 0.4 cm. We believe it is most important to control the sputtering deposition on and near the rounded tip. This appears to be the most active part of the sensing element.

After the inner electrode is applied and fired to the thimble interior, the outer electrode is deposited. As is usual for any thin film deposition, the zirconia surface should be well cleaned before depositing the platinum electrode onto it. It is presumed that any of the normal and accepted cleaning procedures would work as preparation of the surface for sputtering in accordance with this invention. For example, the sensors can be initially cleaned in an ultrasonic degreaser with freon-based solvent and then heated in air to a temperature of at least about 600° C. for 1 hour. The sensors can then be heated again at a temperature of only about 150° C. for about 45 minutes to 2 hours. The thus treated zirconia bodies can then be placed directly in a vacuum chamber for sputtering. If the electrode is not sputtered within 72 hours after the last-mentioned heating, the zirconia bodies should be heated again to 600° C. and 150° C. as discussed.

We currently sputter the electrodes with a model MRC 902 DC magnetron sputtering apparatus obtained from Materials Research Corporation of Orangeburg, N.Y. This apparatus has an elongated but fairly shallow vacuum chamber with provision for two fixed targets disposed over a single anode that is much larger than the targets. The targets will hereinafter be more fully described. However, they essentially are two mutually spaced parallel strips oriented transverse to a rectangular stainless steel anode. The anode is about 35 cm wide, about 50 cm long, and about 2–3 cm thick. Water cooling of the anode is not necessary but may be beneficial for reduced cycle time. We presently choose to use only one target in this apparatus. The targets and anode are in a main chamber adjacent an antechamber having an elevator mechanism that can stack two pallets. We refer to the antechamber as a load-lock. A movable sealing means separates the antechamber from the main chamber. A special carrier is provided for shuttling pallets of substrates from the antechamber into the main chamber for sputtering and then back again. In sputtering, a discharge is first established between a target and the anode. Then the carrier moves the pallet between them. It continues to move in the same direction until out from under the target, whereupon the discharge is discontinued. Carrier speed is adjusted to attain the desired coating thickness.

While one batch of substrates is being coated in the main chamber, another is being removed from the antechamber, a new batch placed in the antechamber, and the antechamber returned to low pressure.

In using the aforementioned apparatus the targets are substantially always maintained under sputtering atmosphere conditions or high vacuum, except for apparatus servicing. To load the apparatus with substrates, a batch of the aforementioned zirconia thimbles are placed on a pallet in the antechamber while the antechamber is sealed from the main chamber and is at ambient pressure. The antechamber is then sealed to the ambient and evacuated to about 100 millitorr. After sputtering in the main chamber is discontinued, the seal between it and the antechamber is opened. The pallet, if any, of workpieces just previously sputtered is shuttled to one level of the antechamber elevator, which picks it off the carrier. The elevator is moved to a next level, and the just-loaded pallet is placed on the pallet carrier. The pallet carrier then moves into the main chamber far enough to close the antechamber-main chamber seal.

After the main chamber is sealed from the antechamber, the antechamber can be backfilled with dry nitrogen to atmospheric pressure and opened to the ambient for reloading. The main chamber is pumped down to below about $5 \times 10^{-6}$ torr. A flow of 75% nitrogen-25% argon by volume is then introduced into the main chamber at a rate of about 75–100 cc per minute, while pumping continues. Pumping is then throttled at a sufficient rate to dynamically maintain a pressure in the main chamber at about 10–20 millitorr. Once pressure in the main chamber is stabilized, a discharge can be established between the target and anode. Pressure is maintained at this level in this way during sputtering, as is usual.

We presently prefer to coat the thimbles in batches of about 280 thimbles. When the thimbles are placed on the pallet, they are all oriented vertically, and thus have parallel axes. Their closed ends are upwardly disposed, with their wider ends resting in recesses directly on the pallet. The pallet we currently use is formed of two rectangular stainless steel plates about 32 cm long and about 32 cm wide. The bottom plate is about 0.4 cm thick. The top plate is about 0.6 cm thick and has an array of holes in it for receiving and uniformly closely spacing the thimbles. These holes, if closely fitting around the thimbles, can also serve as a mask to limit platinum deposition on the thimble flange radial surfaces. For example, the holes can be about 1.33 cm in diameter, preferably in a uniform array of columns and orthogonal rows, both of which are spaced about 0.5–0.6 cm apart. In our apparatus we presently use 15 apertures per row and 18 apertures per column. The lower plate also has a plurality of parallel grooves in its upper surface registered with the rows. The grooves may help to better evacuate the thimble interiors. The two plates of the pallet rest on a U-shaped pallet holder, which is supported by five alumina cylinders, each of which is about 1.3 cm long and 0.6 cm in diameter, which cylinders we refer to as "stand-offs". The stand-offs are, in turn, supported on a wheeled frame-like assembly that serves as a pallet carrier. The pallet carrier supports the pallet about 0.5–1.5 cm above the sputtering anode. However, we do not know if any separation at all is needed.

The pallet carrier has metal wheels which roll directly on the metal base plate of the sputtering chamber. The wheels of the carrier straddle the anode. The anode is 3.01 cm above the chamber base plate and is supported on metal stand-offs which, in turn, are supported on the chamber base plate.

After the antechamber seal is opened, the pallet is transferred onto the pallet carrier and the pallet carrier shuttled to its initial position in front of the target. When so positioned, the thimble closed ends are spaced about 3.8 cm below a planar platinum target surface of a cathode and the pallet is spaced about 0.5–1.5 cm above its anode.

The sputtering target is a rectangular platinum sheet about 12 cm by 38 cm by 0.6 cm bonded to a supporting copper backing plate. The nature of the platinum target is no more critical to this invention than it is to any other sputtering of platinum. The target can be obtained by any commercial source, and preferably provides a high purity platinum surface. While we presently do no prefer it, we recognize that in some instances it may prove to be desirable to include minor amounts of other metals in the platinum target along with the pure platinum, as for example, up to about 5% by weight palladium and/or rhodium. The target is assembled with a cathode that includes water cooling means and a magnet array.

A DC voltage of about 500–800 volts is applied between the target and the anode. The sputtering power supply is then adjusted to provide a DC power between the target and the anode of approximately 13–22 watts/cm$^2$ of target area. No special means are used in the pallet, pallet carrier or anode to heat or cool the thimbles during sputtering. Also, no electrical bias or grounding is used on the pallet assembly. The pallet assembly is allowed to electrically float. After the plasma has stabilized, the pallet carrier moves the pallet through the plasma at a uniform rate of 4 to 5 cm/min. As previously mentioned, the carrier movement rate is adjusted to obtain the desired coating thickness.

Under the foregoing conditions, a porous platinum coating about 1.0–1.5 micrometers thick on the upper ends of the zirconia thimbles will be formed. The thimble closed end will obviously get the greatest thickness of platinum deposit. Side walls on the element will get a correspondingly lesser platinum deposit. We prefer to sputter long enough to produce a coating thickness of about 0.65–1.0 micrometer thick at a point about 0.5 centimeter back from the thimble closed end, along with a coating thickness of about 0.3–0.55 micrometer thick about 2 centimeters back from the thimble closed end.

As mentioned in the process claimed in the aforementioned U.S. Ser. No. 89,264, we too prefer to heat the zirconia thimble after the platinum electrode has been sputtered, to increase electrode adhesion. Adhesion can be increased by heating the electroded thimble at 800° C. in air at atmospheric pressure for about 1 hour. This increase in adhesion can be obtained by heat treatments in air over a rather wide temperature range extending from 600° C. to about 1200° C. However, it should be recognized that heat treatments above about 800° C. tend to open large pores in the coating, about 0.5–5 micrometer in width. If extensive, such heating can sinter the electrode film to such an extent that isolated platinum islands are formed. This is obviously objectionable. Also, heat treating reduces apparent electrode surface area to a value much closer to its geometric surface area. By apparent area we mean surface area as determined by gas adsorption techniques. By geometric surface area, we mean the surface area as calculated from a drawing of the thimble. As discussed in the aforementioned U.S. Ser. No. 89,264 and U.S. Ser. No. 030,747, reducing the high apparent surface area to a lower value by a post-electroding heat treatment somehow does not destroy the advantages of the initial high apparent surface area, so long as the heat treatment is not severe.

Then a porous coating of magnesium-aluminate spinel is flame sprayed onto the platinum electrode, leaving a portion of the electrode uncovered for making of a low resistance electrode connection. The thimble is then directly incorporated into a working sensor without any further treatment, and can be used as assembled.

It is recognized that the flame spraying of a ceramic overcoat onto the thin electrode may drastically alter the physical appearance of the thin film. On the other hand, it does not appear to deleteriously affect controllability of switching response times obtained by this invention. Electrical characteristics attributable to the nature of the electrode as it was initially deposited apparently still remain. The resultant sensor as assembled consistently exhibits fast switching transition times that are similar for rich-to-lean and lean-to-rich and also exhibits a controllability closer to stoichiometry. For example, a rich-to-lean time response of less than 600 milliseconds is regularly obtained in the sensors as assembled. Moreover, more than half of these sensors will consistently have an assembled rich-to-lean time response of less than 200 milliseconds. In recent tests, sensors were made that exhibited switching transition times having a mean value of 120 milliseconds as assembled. These sensors had rich-to-lean time responses no greater than about 1.5 times the lean-to-rich response times. This is generally equal. Controllability for example is regularly obtained to within less than 0.1 air/fuel ratios on the lean side of stoichiometry. Stoichiometry is 14.55:1 under standard conditions. Hence, the sensors control at about 14.65 as assembled. Moreover, the sensor switching transition times and controllability do not appear to significantly change when the sensor is initially used. Accordingly, sensors produced in accordance with this invention do not need to be operationally or artificially aged in order to achieve stability, low response time or better controllability.

The benefits of this invention should be obtained whether or not the electroded thimble is heated in air to increase electrode adhesion and whether or not the electrode is given a porous overcoat. Still further, other porous overcoats can probably be used, as for example the gamma alumina coatings disclosed in U.S. Pat. No. 4,116,883 Rhodes. Also, it may be desirable to use a platinum cermet stripe on the outer surface of the zirconia thimble under the sputtered electrode, at least where the porous overcoat does not cover it, to improve durability. If so, the cermet stripe can be fired at the same time as the inner electrode. Then, our sputtered electrode would be applied.

Further, it is expected that the results of this invention should be obtainable regardless as to the nature of the reference electrode or its method of application. Analogously, they should be obtainable on partially or fully stabilized zirconia having other stabilizing agents than hereinbefore described and even with other solid electrolytes. Further, the principles of this invention should be equally applicable to RF sputtering and to DC sputtering other than magnetron sputtering. Still further, the sputtering conditions of this invention should be useful in a single batch type apparatus having no antechamber, or in a continuous processing apparatus that would include one or more controlled atmosphere chambers before and after the sputtering chamber.

Still further, it was hereinbefore explained that this invention produces a higher yield of sensors having a lower average response time as formed, over sensors produced in accordance with the method of U.S. Ser. No. 89,264. On the other hand, even faster average switching transition times and greater reproducibility may be available, if sensors formed in accordance with this invention are also given a nitrogen aging treatment such as described and claimed in U.S. Ser. No. 030,747.

In this latter connection, it should be recognized that when hundreds of elements are simultaneously electroded in a batch, some are not as good as others. The vast majority of elements will form very good sensors, but some will not. The aforementioned aging treatment of U.S. Ser. No. 030,747 will probably help those sensors which are marginal, and may even improve those that are only slightly better than marginal. However, it is difficult to discern which sensors will benefit from such a treatment and which will not. Since the aging treatment is relatively inexpensive, we prefer to age all of them and insure that optimum characteristics are attained with all sensors.

We also have mentioned that the pallet is left electrically floating. We have not noticed any benefit in applying a special separate bias to it. On the other hand, we have noted that yields of improved devices decreased when stainless steel stand-offs were substituted for alumina stand-offs.

We also hereinbefore mentioned that we believe that the deposition conditions at the closed upper end of the zirconia thimble are most important. It appears that if the deposition conditions are adjusted to obtain a thin black deposit on the zirconia closed end, fastest sensors are obtained. We think the black deposit is or contains chemically reduced zirconia. The deposit should only extend 2-4 mm back from the closed end and be only about 0.5 mm into the original zirconia surface. We are not yet sure of the effect this black layer has on long term, i.e. 50,000 mile, durability. On the other hand, we recognize that if the thimble is blackened completely through its thickness and/or completely along its length, poorer sensors are produced. Changing the stand-offs from ceramic to metal appears to cause too much of this black deposit to be formed. This indicates that inherently there is a controlled amount of current leakage from the pallet during sputtering, notwithstanding the alumina stand-offs. Accordingly, for other apparatus than that disclosed herein, one may prefer to add a controlled resistance path to ground from the pallet, apply electrical bias, or increase electrical isolation in order to attain just the right amount of blackened tip. In retrospect, it may be that the sputtering conditions recited herein coincidentally produce a suitable but as yet undefined electrode microstructure, artifically age the electrode in situ, and controllably reduce the zirconia just enough to improve device performance after the air anneal.

The embodiments of the invention in which an exclusive property or privilege is claimed are defined as follows:

1. In a method of sputtering platinum onto a solid electrolyte body to form an exhaust gas electrode for an electrochemical-type exhaust gas oxygen sensor, the improvement wherein the platinum is sputtered under an atmosphere consisting essentially of more than about 50% by volume of at least one member selected from the group consisting of nitrogen and oxygen and less than about 50% of an inert gas, in proportion effective to provide low sensor rich-to-lean and lean-to-rich switching response times of less than 600 milliseconds with the electrode as deposited.

2. In a method of sputtering platinum onto a vitrified zirconia body to form an exhaust gas electrode for an electrochemical-type exhaust gas oxygen sensor, the improvement wherein the sputtering is performed using an argon atmosphere that contains at least 65% by volume of one member selected from the group consisting of nitrogen and oxygen, whereby low sensor rich-to-lean switching response times of less than 600 milliseconds are obtained that are generally equal to lean-to-rich switching response times, without post-electroding treatments.

3. In a method of sputtering platinum onto a solid electrolyte body to form an exhaust gas electrode for a zirconia, solid-electrolyte exhaust gas oxygen sensor, the improvement wherein the platinum is sputtered under an atmosphere consisting predominantly of nitrogen, the remainder being an inert gas and a target spacing, deposition rate and chamber pressure sufficient to provide a highly porous platinum deposit and a partially blackened zirconia surface under the platinum deposit, whereby sensor switching response time is reduced to below 250 milliseconds as deposited.

4. In a method of sputtering a porous platinum exhaust gas electrode onto a vitrified zirconia thimble for an electrochemical-type exhaust gas oxygen sensor wherein a generally planar platinum target is oriented normal to the axis of a zirconia thimble, the target is spaced at least about 3.0 cm from a closed end on the thimble, and the target is sputtered under an argon atmosphere at a pressure of about 10-20 millitorr and a power of about 13-22 watts/cm$^2$ of target area, the improvement wherein the atmosphere contains more than about 65% by volume of at least one member selected from the group consisting of nitrogen and oxygen and the total pressure is about 10-20 millitorr, effective to increase sensor controllability and to reproducibly obtain sensor rich-to-lean and lean-to-rich switching response times below 250 milliseconds.

5. In a method of sputtering a porous platinum exhaust gas electrode onto a vitrified zirconia thimble for an electrochemical-type exhaust gas oxygen sensor wherein a generally planar platinum target is oriented normal to the axis of a zirconia thimble, the target is spaced about 3.0–5.0 cm from a closed end on the thimble, a thickness of at least about 0.65 micrometer is applied to the thimble end and the target is sputtered under argon at a pressure of about 10–20 millitorr and a DC power of about 13–22 watts/cm$^2$ of target area, the improvement wherein the platinum is sputtered in an atmosphere consisting essentially of about 65–75% by volume nitrogen and the balance argon at a total pressure of about 10–20 millitorr, effective to increase sensor controllability and to reproducibly obtain low and symmetrical sensor rich-to-lean and lean-to-rich switching response times below 250 milliseconds without post-electroding electrolytic or heat treatments.

* * * * *